(12) United States Patent
Lund et al.

(10) Patent No.: US 9,074,970 B2
(45) Date of Patent: Jul. 7, 2015

(54) METHOD FOR FATIGUE ASSESSMENT OF ROLLING BEARING

(75) Inventors: Thore Lund, Göteborg (SE); Karin Rydén, Göteborg (SE)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 14/009,975

(22) PCT Filed: Mar. 28, 2012

(86) PCT No.: PCT/SE2012/000046
§ 371 (c)(1),
(2), (4) Date: Oct. 4, 2013

(87) PCT Pub. No.: WO2012/138275
PCT Pub. Date: Oct. 11, 2012

(65) Prior Publication Data
US 2014/0026674 A1    Jan. 30, 2014

(30) Foreign Application Priority Data
Apr. 4, 2011    (SE) ........................ 1100243

(51) Int. Cl.
*G01N 3/24*    (2006.01)
*G01M 13/04*    (2006.01)
(Continued)

(52) U.S. Cl.
CPC ................. *G01N 3/24* (2013.01); *G01M 13/04* (2013.01); *G01M 13/045* (2013.01); *F16C 19/522* (2013.01); *F16C 33/416* (2013.01); *F16C 23/086* (2013.01); *F16C 33/40* (2013.01)

(58) Field of Classification Search
CPC ...... G01N 3/24; G01M 13/045; G01M 13/04; F16C 33/40; F16C 33/416; F16C 23/086; F16C 19/522

USPC ............. 702/34, 42, 35, 43; 73/593, 577, 841
See application file for complete search history.

(56) References Cited

U.S. PATENT DOCUMENTS 6,573,710 B1    6/2003    Santos et al.
6,725,720 B2 *  4/2004    Kiuchi et al. ................... 73/593
(Continued)

FOREIGN PATENT DOCUMENTS

EP    102995 A1    5/2001
EP    1184813 A2   3/2002
(Continued)

OTHER PUBLICATIONS

Thore B. Lund, "Sub-Surface Initiated Rolling Contact Fatigue—Influence of Non-Metallic Inclusions, Processing History, and Operating Conditions," Journal of ASTM International, vol. 7, No. 5.

*Primary Examiner* — Lisa Caputo
*Assistant Examiner* — Jonathan Dunlap
(74) *Attorney, Agent, or Firm* — Bryan Peckjian; SKF USA Inc. Patent Dept.

(57) ABSTRACT

The present invention related to a method, and an apparatus arrangement, for determining a fatigue limit for rolling contact initiated fatigue of a rolling bearing. The method comprises running a rolling bearing while being exerted to a load which generates sub-surface transformations in a rolling element contact zone of the outer or inner ring. Furthermore a set of sub-surface transformations in the contact zone along a raceway portion of the rolling bearing is identified and measured and used for generation of a parameter data set, wherein a fatigue parameter value representative of a predicted fatigue limit for the rolling bearing is determined based on the generated data set of sub-surface transformations.

20 Claims, 7 Drawing Sheets

(51) Int. Cl.
*F16C 19/52* (2006.01)
*F16C 33/41* (2006.01)
*F16C 23/08* (2006.01)
*F16C 33/40* (2006.01)

(56) References Cited

U.S. PATENT DOCUMENTS

2002/0105445 A1   8/2002   Shirai et al.
2007/0044543 A1*  3/2007   Umeda et al. ................ 73/76
2013/0006542 A1*  1/2013   Matsubara et al. ............ 702/34
2013/0298704 A1* 11/2013   Ito et al. ...................... 73/865.8

FOREIGN PATENT DOCUMENTS

| EP | 1211500 A1 | 6/2002 |
| EP | 1557676 A1 | 7/2005 |
| EP | 1748371 A1 | 1/2007 |
| JP | 20030471 A | 11/2000 |
| JP | 1215140 A | 10/2011 |
| WO | 2007077389 A2 | 7/2007 |
| WO | 2008000285 A1 | 1/2008 |

* cited by examiner

METHOD FOR FATIGUE ASSESSMENT OF ROLLING BEARING

CROSS REFERENCE

This application is the U.S. National Stage of International Application No. PCT/SE2012/000046 filed on Mar. 28, 2012, which claims priority to Swedish patent application no.1100243-3 filed Apr. 4, 2011.

FIELD OF THE INVENTION

The present invention relates to a method, or a test method, for determining a fatigue limit for rolling contact initiated fatigue of a rolling bearing. The method comprises running a rolling bearing comprising a plurality of rolling elements arranged between an outer and an inner ring, while the rolling bearing is exerted to a load which generates sub-surface transformations in a rolling element contact zone of the outer or inner ring.

The present invention further relates to an apparatus arrangement for testing a rolling bearing for the purpose of determining a fatigue limit for rolling contact initiated fatigue, wherein the apparatus arrangement comprises a test rig for running a rolling bearing which is arranged to exert a load on the rolling bearing for generation of sub-surface transformations in a rolling element contact zone of the outer or inner ring of the rolling bearing.

The method and apparatus arrangement according to the present invention may for example be used for testing a rolling bearing, or a set of rolling bearings, of a specified type, and to evaluate the properties of the that type in order to determine a fatigue limit for rolling contact initiated fatigue.

BACKGROUND ART

During operation, a rolling bearing that e.g. is well lubricated, properly aligned and sufficiently protected from effects of abrasive or moisture during operation may still fail from rolling contact fatigue. This type of failure is normally observed as flaking off of metallic particles from surface of the raceway of an inner or outer ring of a bearing, or from the surface of the rolling elements. The flaking typically commences as a sub-surface crack below the surface which propagates to the surface whereat a pit or a spall is formed in the surface exerted to the load.

To improve the use and benefit of rolling bearings, it is important to be able to predict length of service, life, endurance, that can be achieved from a bearing in a specific application. However, due to the rolling contact fatigue, the ability to make this type of predictions is hampered.

In order to predict bearing fatigue parameters, statistical procedures have been established for e.g. theoretical life predictions of bearing fatigue life. Such predictions, using e.g. Weibull statistics, are based on large quantities of data which are collected by experimental techniques encompassing large populations of apparently identical rolling bearings which are subjected to apparently identical load, speed, lubrication and environmental conditions.

Methods for testing life, or endurance, parameters of bearings are further used to evaluate and assess the bearing material and manufacturing processes of bearings, such as surface forming and heat treatment processes. However, the assessment of initiation and development of sub-surface initiated fatigue in rolling contact applications is time consuming, costly and difficult to measure and predict due to e.g. the spread in experimental fatigue data. Known methods that are used encompass large expenditures and time in order to evaluate the usefulness of steels intended for bearing steel component production, and all of these methods are hampered by the use of numerous bearings that are tested under conditions that are beyond the actual conditions of specific applications. In other words, even though accelerated techniques are utilized, a large amount of bearings must be tested for relatively long times in order to achieve valid estimates of bearing life, wherein the testing costs are closely linked to the manufacturing cost of the bearing test specimens.

SUMMARY OF THE INVENTION

In view of the above-mentioned and other drawbacks of the prior art, a general object of the present invention is to provide a method for determining a fatigue limit for rolling contact initiated fatigue of a rolling bearing, which method comprises running a rolling bearing comprising a plurality of rolling elements arranged between an outer and an inner ring, while the rolling bearing is exerted to a load which generates sub-surface transformations in a rolling element contact zone of the outer or inner ring. The method further comprises identifying a set of sub-surface transformations in the contact zone along a raceway portion of the rolling bearing, and measuring, for each sub-surface transformation in the raceway portion, a position parameter value representative of sub-surface depth and a stress parameter value representative of contact stress in the contact zone. Moreover, the method comprises generating a data set of sub-surface transformations comprising the position parameter values in relation to the stress parameter values for each sub-surface transformation, and determining a fatigue parameter value representative of a predicted fatigue limit for the rolling bearing based on the generated data set of sub-surface transformations.

Advantageously, the present invention realizes an improved method to evaluate the resistance of e.g. steel to rolling contact fatigue in rolling bearings, which method provides a solution and definition of a rolling contact fatigue limit. In particular, the method provides a more efficient, and simplified low cost possibility to, with single or considerably fewer test samples, realize a prediction of the fatigue limit for the combination of specified relative bearing properties, such as selected bearing steel material and heat treatment selected for manufacturing, the resistance of the steel to sub-surface initiated fatigue and an estimate of the combined steel and heat treatment response to contact stresses.

Put in slightly different words, the present invention is based on the realization that, by providing a test method for determining a fatigue limit for rolling contact initiated fatigue of a rolling bearing, which method enables statistical evaluation of the initiation of and development sub-surface transformations, such as initiation and progression of butterflies and butterfly wing formations in single test samples, meaningful results and predictions is provided faster and in a more efficient manner. Furthermore, by defining a relationship between contact stress and sub-surface initiated fatigue along a raceway portion of the rolling bearing, evaluation of stress conditions between different stress levels, such as stress conditions from very high, or maximum, to zero, or other suitable ranges of stress conditions, is realized in single test samples. Hence, compared to known test methods of prior art which are indirect and do not provide a direct prediction of rolling contact fatigue limit, the present method facilitates and expedites a prediction and definition of the relationship between contact stress and sub-surface initiated fatigue.

When e.g. evaluating the possibilities of introducing a new steel making and processing method for rolling bearing applications, the method for determining a fatigue limit according to an embodiment of the present invention may advantageously be used to compare a number of factors, such as different steel compositions or different heat treatments of the same steel composition. Hence, the method advantageously allow for fast prediction and relative comparisons between various parameters of bearing samples.

For example, by generating a data set comprising position parameters values and stress parameters values associated with separate sub-surface transformations, the method allows for extraction of useful relationships between contact stress and sub-surface transformations in the contact zone which allow for fatigue limit predictions. It is e.g. possible to, for a single test object, relate the formation of sub-surface structural transformation to the stress experienced at the location of a stress raiser generating it, and determine a fatigue limit prediction based on those relations. For example, the determination of the a fatigue limit prediction may be realized by analyzing the data set in order to identify the distribution of sub-surface transformation and dependencies of the generated sub-surface transformations in relation to depth and contact stress. The data-set of sub-surface transformation parameter values may be analytically, numerically or graphically analyzed, e.g. by plotting a contact stress/sub-surface depth distribution. Hence, the data set may advantageously be used for e.g. defining contact stress/depth plots, or spaces, which is representative of the characteristics of the generated and identified sub-surface transformations of the tested bearing. For example, a test of a single test bearing may involve the generation of at least 20 sub-surface transformations, or at least 50, at least 100, or at least 500 individual sub-surface transformations in the contact zone of the raceway portion of the outer or inner ring.

According to exemplifying embodiment of the present invention, the method further comprises determining at least one shear stress level parameter value representative of shear stress in the contact zone, wherein the shear stress level parameter depends on contact zone depth and exerted contact stress. Hence, in single test bearing samples, a data-set representative of parameters values relating to depth below surface, stress condition, associated with a plurality of sub-surface transformation may be used in combination with the determined shear stress level parameter value for determining a fatigue limit. According to an embodiment of the present invention, the step of determining the fatigue parameter value further comprises comparing the at least one shear stress level parameter value with the data set of sub-surface transformations. For example, test data in the form of the generated data-set may be assessed and evaluated in relation to shear stress levels by using e.g. a contact stress-depth plot in combination with one or a plurality of shear stress levels. By analyzing the parameters values associated with the sub-surface transformations, prediction of the stress limit that needs to be exceed in order to initiate developing of sub-surface transformations, or damages, is possible. Prediction of the stress limit that needs to be exceeded to initiate sub-surface transformation may be determined by analytical, graphical or numerical, analysis of the data set.

The fatigue parameter value is, according to an embodiment, determined based on a shear stress level parameter value below which none, or less than 5%, or less than 10%, of the sub-surface transformations generated during running of the rolling bearing are formed. Hence, for a single test object, the fatigue parameter may advantageously be predicted based on collected parameter data associated with the identified sub-surface transformations and a determined shear stress level. In other words, a fixed shear stress level representative of a fatigue limit may be determined wherein essentially all, or 95%, or 90% of the identified sub-surface transformation associated with and described in the data set are formed during conditions exceeding the fixed stress level. Hence, in determining a fatigue limit, the method advantageously accounts for a range of sub-surface transformation occurring at different depth and for different stress conditions in a single bearing.

According to further exemplifying embodiment of the present invention, the step of determining the fatigue parameter value further comprises determining a set of shear intervals of consecutive shear stress level values, determining, for each shear interval, a frequency parameter value representative of the number of sub-surface transformations situated within each shear interval, and estimating the fatigue parameter value by approximating the relationship between the set of shear intervals and the frequency parameter. Hence, an efficient approach for analyzing and derive fatigue limit predictions is provided. For example, a contact stress/depth plot, or space, defined by the data set, may be augmented with shear stress curves derived for the specific test conditions used during running of the test bearing specimen, which curves defines separate groups, or intervals, in the data set. Hence, based on the collected data of sub-surface transformations, the frequency of sub-surface transformation located with each shear stress group is identified and used for numerical, analytical, graphical, approximation of fatigue limit. For example, curve fitting, various numerical interpolation approaches, or least square techniques, may be used for determining trends and curves based on the frequency of sub-surface transformations in relation to contact stress/depth data set.

Furthermore, according to an embodiment of the invention, the exerted load develops a rolling contact stress, or maximum rolling contact stress, above at least 3000 MPa, or at least above 4000 MPa, or at least above 4500 MPa. Hence, high contact stresses are provided which advantageously generate an accelerated initiation and development of sub-surface transformations. For example, a self-aligning ball bearing, with point contact between rolling elements and an outer spherical raceway, may be run in a test rig at 1800 rpm and with radial load of 18 kN generating an outer ring contact stress value of 4.9 GPa. A relatively high radial load, such as between 15 and 20 kN, advantageously provides high contact stress conditions in the raceway which will generate a statistically relevant amount of sub-surface transformation. This further allows for statistically improved and relevant results in term of predicted fatigue limit, either for a single test object, or of a set of a two, five, or a few test objects.

The load may according to an embodiment be a radial point load, or a load acting in an essentially circular, or point, shaped area. Furthermore, the load may be fixed in relation to the rolling element contact zone of either the outer or the inner ring depending of which one is rotating. In other words, the load is fixed in relation to the contact zone of the non-rotating ring in which the generation of sub-surface transformations takes place. This means that the contact stress exerted in the contact zone of the raceway will differ with respect to the location, or distance, along the raceway portion of the in relation to the load contact point.

For example, according to an embodiment, the raceway portion comprises a maximum load point, or maximum contact stress point, and the raceway portion extends, from the maximum load point, at least one quarter of the complete raceway. Hence, essentially all of the sub-surface transformation generated in the portion may be identified and analyze, wherein the extension of the raceway portion comprises a suitable contact stress gradient. In particular, depending on the exerted load the and operating properties, such as preload etc., the contact stress amount may vary from a maximum value at the load contact point to a lower level, or minimum value, at e.g. a quarter distance of the raceway from the load contact point.

According to a further exemplifying embodiment, the method further comprises cutting through, or grind to, the contact zone along the raceway, wherein the cut surface, or a grind surface, coincides with a geometrical plane having a normal direction coinciding with an axial direction of the rolling bearing. By cutting, or grinding, the bearing into the contact zone such that a cross-section surface having a normal coinciding with the axial direction of the bearing, the sub-surface transformations along the raceway portion may be identified and measured in an efficient manner. For example, according to an advantageous embodiment, the step of identifying and measuring the sub-surface transformation comprises visual or optical inspection, such as high magnification optical inspection, microscopy, scanning electron microscopy, etc. Further inspection methods include metallurgical and dimensional based measuring and examining, and/or chemical evaluation methods.

In yet an embodiment of the present invention, the method comprises monitoring the occurrence of fatigue failure during running of the rolling bearing, and running the rolling bearing until a predetermined fatigue parameter is reach. Operating parameter used to indicate failure may be vibrations, noise, and/or temperature, etc.

Typically, but not limited to this use, the method according to an embodiment of the present invention is used for determining a fatigue limit for rolling contact initiated fatigue of a ball bearing, such as a self-aligning ball bearings. In particular, the spherical geometry of e.g. the outer ring raceway enabling self-aligning capabilities, imply point contacts between the balls and the raceway with sufficiently high contact stress levels. It is noted, that a point contact typically refers to a specific essentially circular shaped area at which the ball and raceway meet, which may be compared with a bearing comprising roller elements having larger ellipse shape contact areas.

According to another aspect of the present invention, it relates to a computer program comprising program code means for performing the method according to any one of the described embodiments of the present invention, when the program is run by at least one micro processor.

According to yet another aspect thereof, the present invention relates to an apparatus arrangement for testing a rolling bearing, which arrangement comprises a test rig for running a rolling bearing comprising a plurality of rolling elements arranged between an outer and an inner ring. The test rig is arranged to exert a load on the rolling bearing for generation of sub-surface transformations in a rolling element contact zone of the outer or inner ring. Moreover, the apparatus arrangement comprises a measuring device arranged to identify a set of sub-surface transformations in the contact zone along a raceway portion of the rolling bearing, which measuring device is further arranged to measure, for each sub-surface transformation in the raceway portion, a position parameter value representative of sub-surface depth and a stress parameter value representative of contact stress in the contact zone, and a control unit configured to collect parameters values and generate a data set of sub-surface transformations comprising the position parameter values in relation to the stress parameter values for each sub-surface transformation, which control unit is further configured to determine a fatigue parameter value representative of a predicted fatigue limit for the rolling bearing based on the generated data set of sub-surface transformations.

Advantageously, the apparatus arrangement according to the present invention allows for improved evaluation and assessment of the resistance of e.g. steel to rolling contact fatigue in rolling bearings. Furthermore, the apparatus enables an efficient and improved approach of defining a rolling contact fatigue limit. In particular, the apparatus allows for a more efficient, and low cost possibility to, with single or considerably fewer test samples, realize a prediction of the fatigue limit for the combination of specified relative bearing properties, such as selected bearing steel material and heat treatment selected for manufacturing, the resistance of the steel to sub-surface initiated fatigue and e.g. an estimate of the combined steel and heat treatment response to contact stresses. Furthermore, the apparatus arrangement is further advantageous in similar manners as and may be adapted in correspondence with the method and method embodiments according to the present invention.

Other objectives, features, and advantages of the present invention will appear from the following detailed disclosure, from the attached dependent claims as well as from the drawings.

BRIEF DESCRIPTION OF DRAWINGS

The present invention will now be described in more detail, with reference to the appended drawings showing at least one exemplifying embodiment of the invention, wherein.

DETAILED DESCRIPTION OF EMBODIMENTS OF THE INVENTION

Figure 1A:
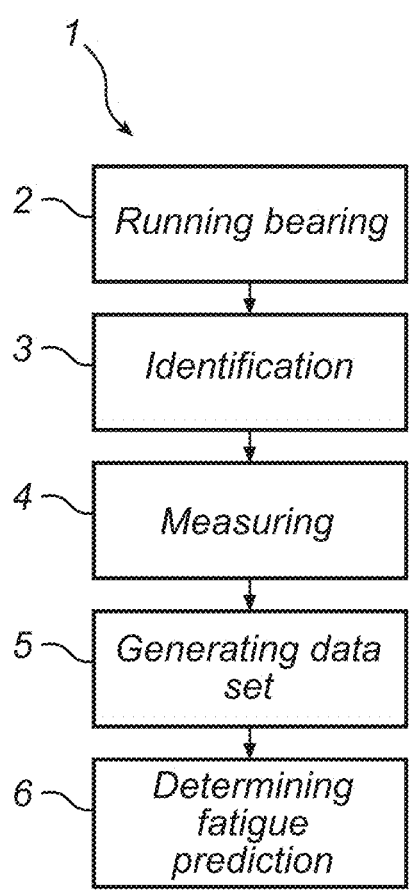
FIG. 1a is a flow chart schematically illustrating an embodiment of the method according to the present invention.

In the drawings, similar, or equal elements are referred to by equal reference numerals. The drawings are merely schematic representations, not true to scale and should not be considered as limiting the scope of the invention.

Figure 1B:
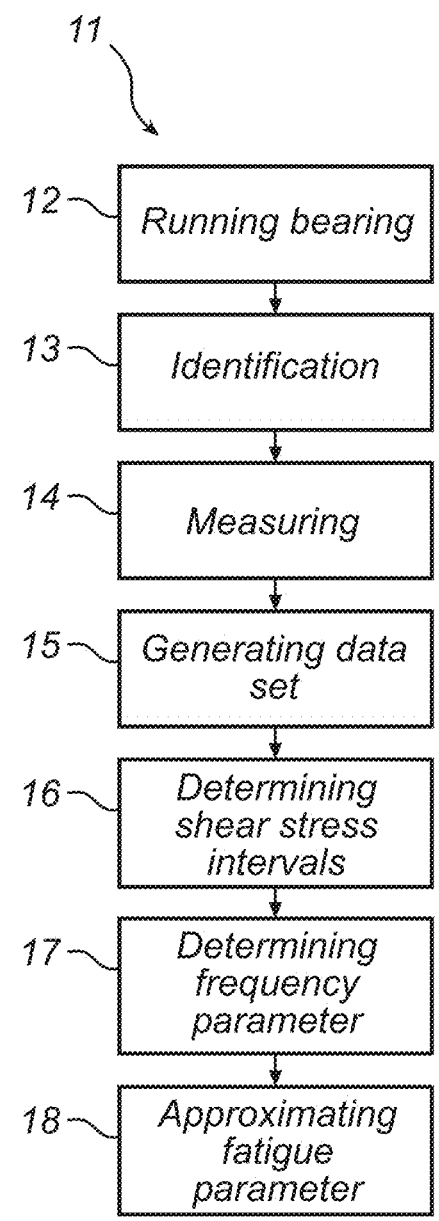
FIG. 1b is a flow chart schematically illustrating an embodiment of the method according to the present invention.

In FIG. 1a-b two different method embodiments 1 and 11 according to the present invention are illustrated in schematic flow charts. With reference to FIG. 1a, in an initial running bearing step 2, a test bearing is run in a test rig, such as an SKF R-2 test machine, wherein the test bearing is subject to a mechanical load which generates sub-surface transformations in the raceway contact zone. The contact zone is formed of the three dimensional volume of the raceway material which is subject to internal stress and shear stress conditions generated and initiated at the e.g. the point shaped rolling contact area between a ball shaped rolling element and the raceway. Typically, the test bearing is run until the occurrence of spalling or sub-surface initiated fatigue failure, or until intentional suspension of the running procedure. After running, in an identification step 3, the contact zone along the raceway of the outer, or inner, ring of the test bearing is inspected, wherein a set of statistically relevant number of sub-surface transformation, such as butterfly formations generated by inclusions, are identified. Identification may e.g. be done by different techniques comprising optical, or visual, examination of the internal structure of the contact zone of a portion of the raceway.

In a measuring step 4, for each sub-surface transformation in the examined raceway portion, a position parameter value representative of sub-surface depth and a stress parameter value representative of contact stress in the contact zone are measured. For example, the position of each structural feature generated by sub-surface transformation is recorded with regards to its depth into the raceway and to its circumferential position in relation to the applied load. Furthermore, the size of inclusions generating butterflies and the maximum (one-sided) size of the wing generated may by measured and recorded by light microscopy examination at e.g. 500× magnification.

For example, the contact zone along the raceway portion of the outer or inner ring is examined on longitudinal "Melander" cuts which extend through the raceway contact zone. Moreover, the position and stress parameter values for each sub-surface transformation may be measured directly after identification of each transformation. Alternatively, a set of sub-surface transformations are identified in a first step after which parameters values associated with each separate sub-surface transformation is measured in a later step.

As further illustrated in FIG. 1a, the method comprises a generating data set step 5, in which a data set of sub-surface transformations comprising the position parameter values in relation to the stress parameter values for each sub-surface transformation is generated. Hence, the collected data is compiled into a data set comprising parameter value information which is used for defining a relationship between contact stress and sub-surface initiated fatigue along a raceway portion of the rolling bearing. Moreover, it allows for evaluation of stress conditions between different stress levels, such as stress conditions from very high, or maximum, to zero, or other suitable ranges of stress conditions, is realized in single test samples. For example, the generated data set comprises a set of first values representative of the position parameter indicative of raceway depth of each one of the set identified sub-surface transformations, and a set of corresponding second values representative of the stress parameter which indicates the contact stress value associated with the set of identified sub-surface transformations, wherein the stress value is determined by the distance, or angular distance, of the sub-surface transformations to a load contacting point on the raceway where mechanical load is applied. The generated data set may further comprises additional parameters values associated with the sub-surface transformations, such as butterfly with growth, lateral or axial location of the sub-surface transformation in relation to a longitudinal extension of the principal raceway direction, direction of sub-surface growth, general operating conditions of the test method, or type of sub-surface transformation.

As further shown in FIG. 1a, the method 1 comprises a determining fatigue prediction step 6, in which a fatigue parameter value representative of a predicted fatigue limit for the rolling bearing is determined based on the generated data set of sub-surface transformation. In other words, the data set of parameter values retrieved from the single bearing test object may be analyzed in order to determine e.g. a contact stress value, internal shear stress value, or equivalent static bearing load value indicative of a predicted fatigue limit for the tested bearing type. Hence, an efficient, versatile and accelerated method for predicting, or comparing, fatigue properties of a single, or a set of, bearings is provided.

With reference to FIG. 1b, the method 22 for determining a fatigue limit for rolling contact initiated fatigue of a rolling bearing comprises similar initial operational step as described with reference to FIG. 1a, i.e. the step of running bearing 12, identification 13 of sub-surface transformation, measuring 14 parameter values of the sub-surface transformation, and generating data set 15. As further illustrated, the method 11 comprises the step determining shear stress level intervals 16, wherein suitable shear stress value intervals are determined and used for analyzing and mapping of the parameter values in the data set. In particular, the shear stress intervals are used for grouping the sub-surface transformations based on their associated parameter values. As illustrated in FIG. 1b, this is performed in a determining frequency parameter step 17, in which a frequency parameter value representative of the number of sub-surface transformations situated within each shear interval is determined. Based on the frequency parameters, the method 11 further comprises an approximating fatigue parameter step 18 comprising an estimation of a fatigue parameter value by approximating the relationship between the set of shear intervals and the frequency parameters.

Figure 2A:
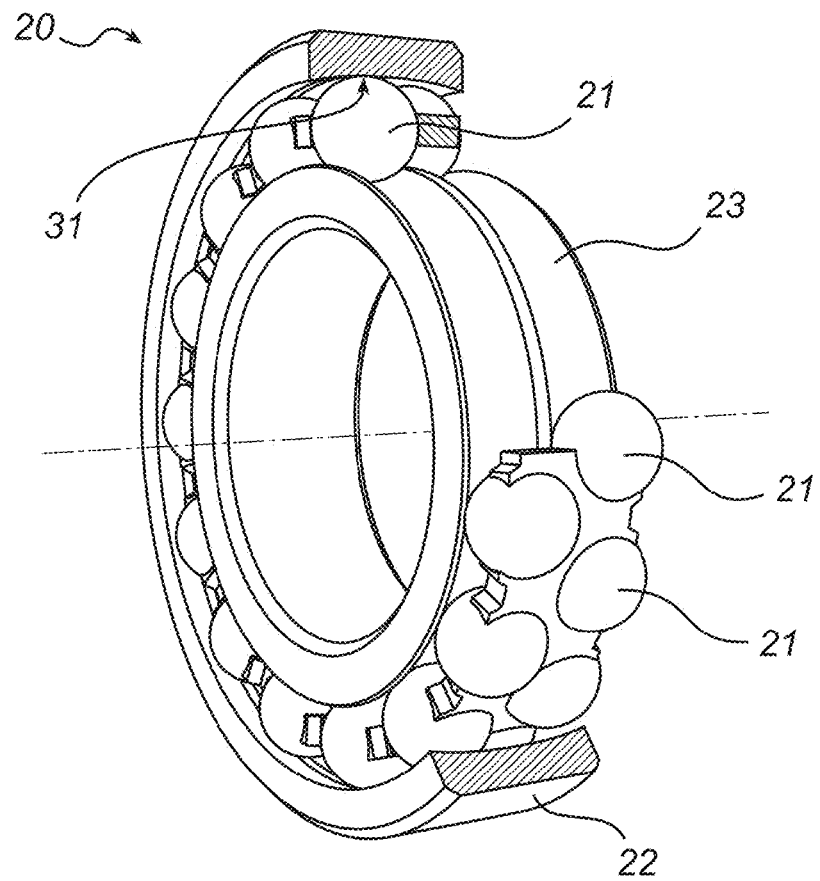
FIG. 2a schematically illustrates a perspective cut out view of a self-aligning ball bearing.

In FIG. 2a, a perspective cut out view of a self-aligning ball bearing 20, is schematically illustrated. In particular, the ball bearing 20 constitutes a suitable test bearing appropriate for fatigue testing and prediction according to the present invention. The ball bearing 20 comprises a plurality of rolling elements in the form of balls 21 arranged in two adjacent rows between an outer 22 and an inner ring 23. Considering the geometry of the ball bearing 20, it comprises an inner ring raceway 30 having a groove which provides an increased rolling contact area between the balls 21 and the inner ring 23. Hence, a load applied during the testing is distributed over a relatively large area which means that a low, typically statistically non-relevant, number of sub-surface transformation will be generated in the inner ring. The rolling contact between a raceway 31 of the outer ring 23 and the balls, however, forms a small point contact which focuses the applied load onto the raceway 31 which increases the generation of sub-surface transformation. According to embodiments of the method according to the present invention, it is used for testing bearings having a geometry enabling sufficiently high contact stresses, or normal stresses, e.g. in the regime of 3000-6000 MPa. For example, suitable rolling bearing types includes, but is not limited to, bearing having single, two, and a limited number of point contacts between the rolling element and the inner or outer ring.

Figure 2B:
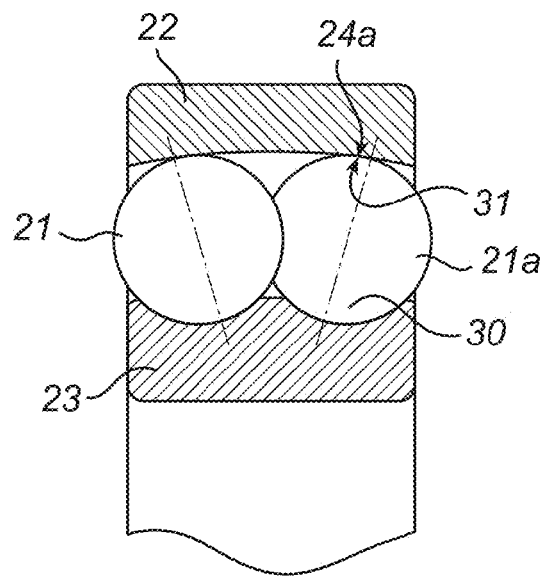
FIG. 2b schematically illustrates a cross-sectional view of a self-aligning ball bearing.

In FIG. 2b, a cross-sectional view of the self-aligning ball bearing 20, is schematically illustrated. As shown, a radially inner side of the outer ring 23 comprises a curved, or spherical, cross-sectional shape wherein the rolling contact area between the ball 21a and the raceway 31 defines a contact zone 24a in which stress and shear stress are generated due to the applied load. Hence, the contact zone comprises a volume wherein sub-surface transformations mainly initiate and develop at a given depth inside the outer ring below the raceway 31 contact area, typically at the location of maximum shear stress.

Figure 3:
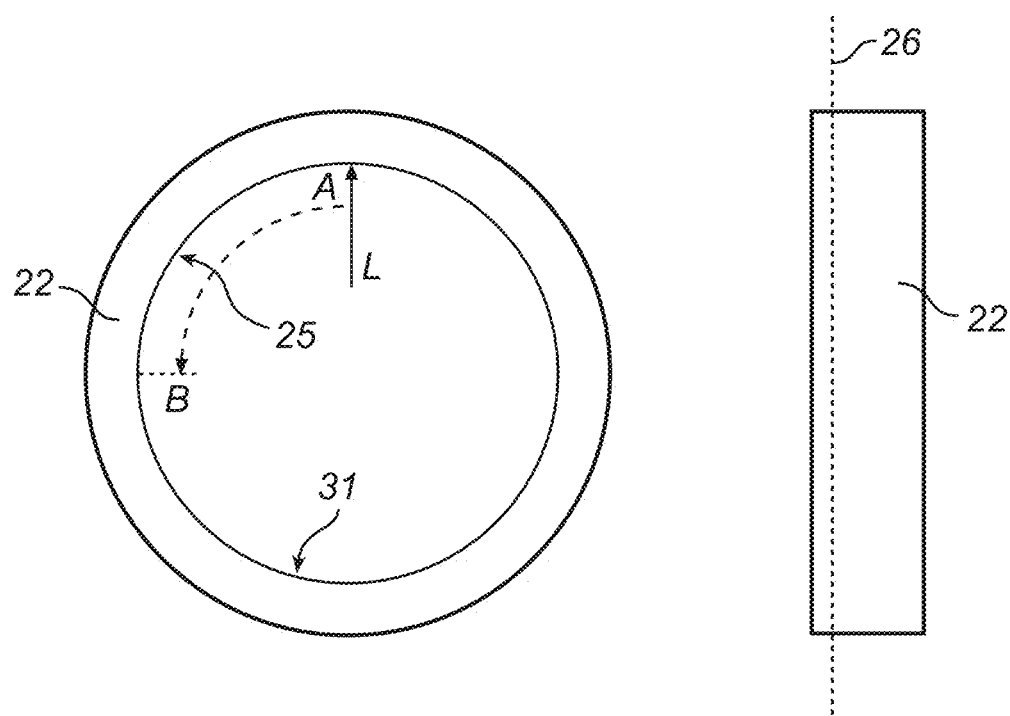
FIG. 3 schematically illustrates two side views of an outer ring of a bearing for testing according to an embodiment of the method according to the present invention.

FIG. 3 schematically illustrates two side views of an outer ring 22 of a bearing for testing according to an embodiment of the method. In the left view, a load L applied to the bearing during testing, is illustrated. The load is fixed in the relation to the tested outer ring 22 and defines a maximum load point indicated by A. The contact stress generated by the load L decrease in a direction towards a low load point, indicated by B. After running the bearing in a test rig, a portion 25 of the raceway defined between the maximum load point A and the low load point B is examined for identification and measuring of sub-surface transformations. As illustrated, the portion of the raceway 25 corresponds to an angular distance of 90 degree. However, the raceway portion may correspond to an angular distance, in relation to the maximum loading point A, in the range between 30 and 150 degrees, between 45 and 135 degrees, or between 70 and 110 degrees. Alternatively, data from sub-surface transformation along the full length of the raceway 31 may be collected.

In the right view of FIG. 3, the radially outer side of the outer ring 22 is illustrated, wherein, after running the bearing in the test rig, the central raceway regions may be examined by cutting a Melander cut as indicated by 26, hence providing a cross-sectional view of the contact zone and raceway of the tested bearing. The cut may be provided by separating the outer ring into two parts along 26, or by removing material, e.g. by grinding axially into the outer ring in a planar manner such that a inspection surface extending in a plane having a normal direction coinciding the axial direction of the outer ring 22 is provided.

Figure 4:
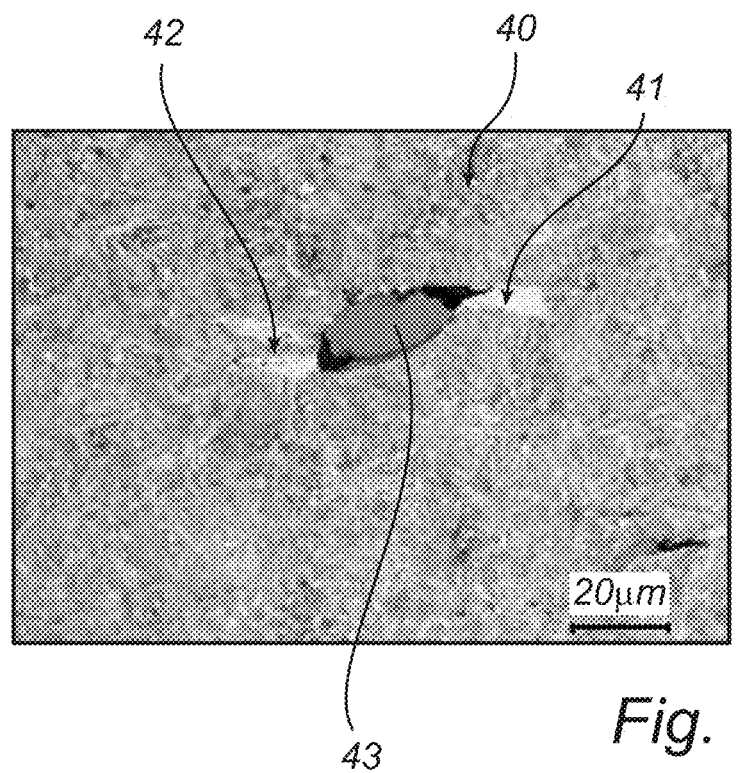
FIG. 4 schematically illustrates an exemplifying sub-surface transformation generated in the contact zone along the race way of a bearing.

FIG. 4 illustrates an exemplifying sub-surface transformation 40 generated in the contact zone along the race way of a bearing during testing according the present invention. The transformation 40 constitutes a typical butterfly having wing formations 41 and 42. Furthermore, the size and composition of an inclusion 43 are typical parameters that drive the development of micro-crack associated butterfly wing formations 41 and 42. Typically, sub-surface transformations, such as butterflies, occur at depth coinciding with the depth of the maximum shear stress level, which level is considered the main operative stress driver for micro-crack developments in the contact zone.

Figure 5:
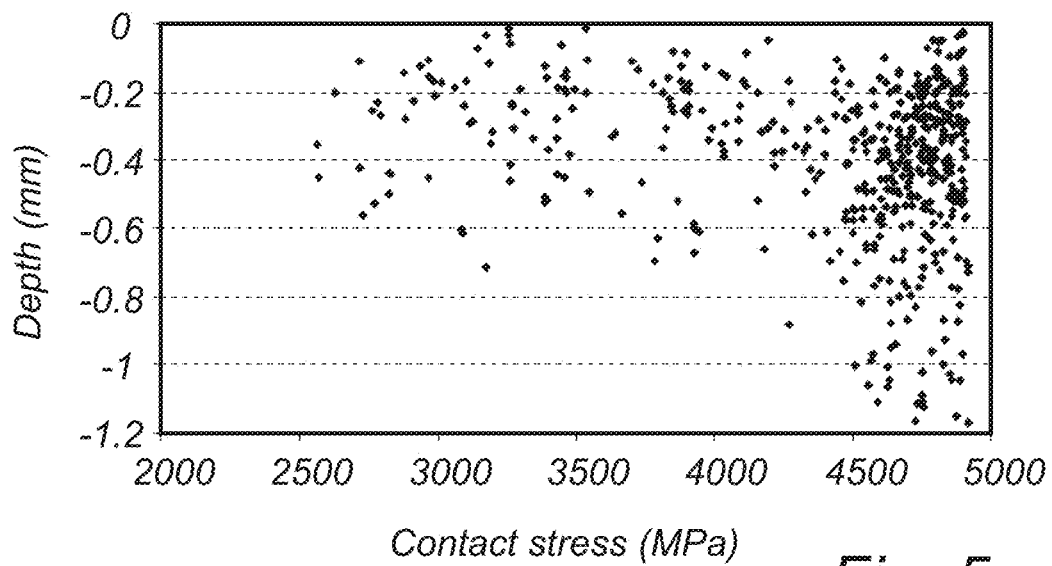
FIG. 5 schematically illustrates a graphical representation of a generated data set of sub-surface transformation parameter values according to an embodiment of the method according to the present invention.

In FIG. 5, a graphical representation of an exemplifying generated data set of sub-surface transformation parameter values according to an embodiment of the method according to the present invention, is schematically illustrated. The position and stress parameter values of each sub-surface transformation identified in the test method have been plotted into a contact stress/depth-diagram, wherein each dot is representative of a sub-surface transformation. The vertical axis is representative of the position parameters which corresponds to how deep the sub-surface transformations are located into the contact zone, while the horizontal axis corresponds to stress condition generated by the applied mechanical load. In more detail, the applied load generated a maximum contact stress of 4900 MPa at the maximum loading point L as indicated with reference to FIG. 3. As can be seen from the plotted data, an increased number of sub-surface transformations have been generated in close proximity to the maximum loading point. As can be further derived from distribution of the data set of sub-surface transformations in the plotted contact stress/depth-diagram, sub-surface transformation having the greatest depth are also located in close proximity with the maximum loading point at the right hand side of the diagram.

Figure 6:
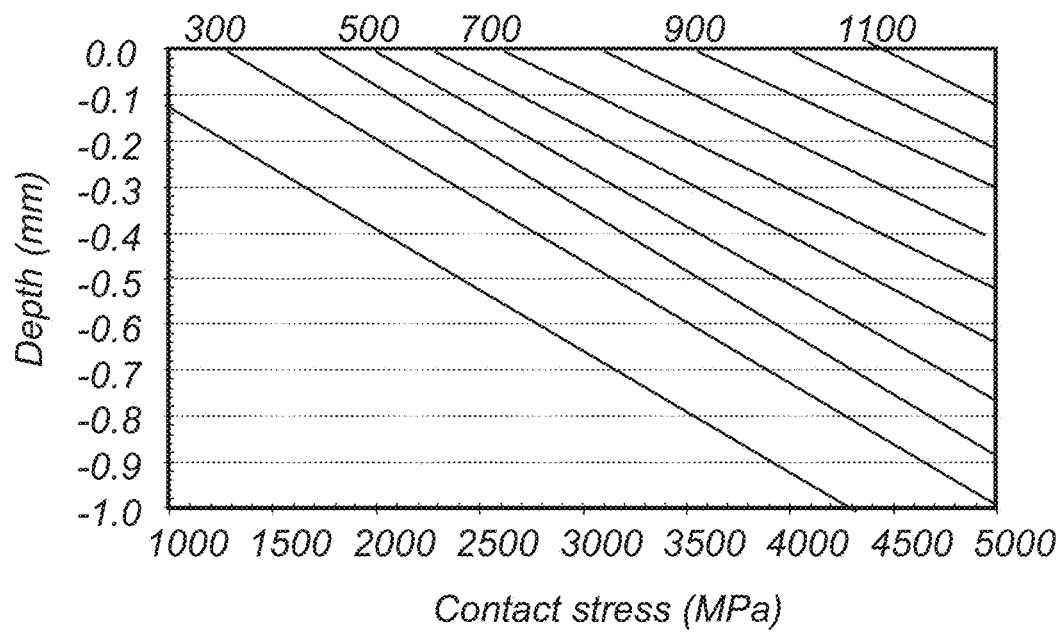
FIG. 6 graphically illustrates determined shear stress levels in a contact stress/depth-diagram according to an embodiment of the present invention.

FIG. 6 graphically illustrates exemplifying shear stress level parameter values in a contact stress/depth-diagram according to an embodiment of the present invention. The shear stress level parameter values are representative of shear stress in the contact zone and depend on contact zone depth and exerted contact stress. The shear stress level values are plotted in the range between 200 and 1100 MPa, as indicated by the upper vertical axis. For example, a fatigue limit based on the information contained in the plotted data set of sub-surface transformation may be provided by identification of a suitable shear stress level value at which no sub-surface transformation are formed.

With reference to FIG. 7 and FIG. 8, two applications of the invention are presented by schematically and graphically illustrating data of sub-surface transformations and fatigue limit approximations from a first and a second exemplifying test according to an embodiment of the method. In more detail, for evaluation of the possibilities of introducing a new steel making and processing method for rolling bearing applications, the test method and the evaluation procedure is used to compare a number of factors.

Figure 7A:
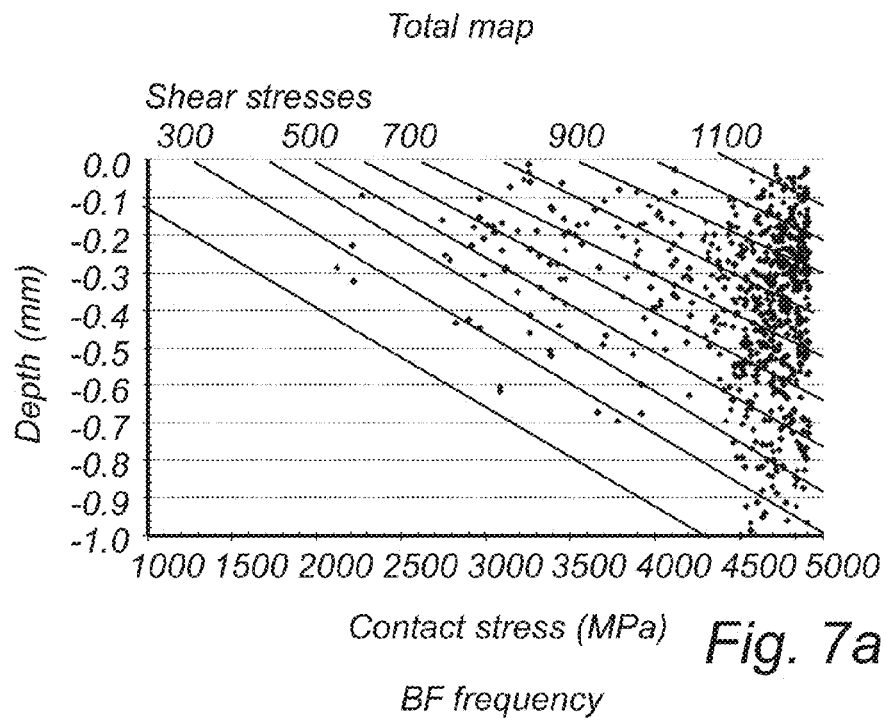
FIG. 7a-c schematically and graphically illustrate data of sub-surface transformations and fatigue limit approximations based on a first exemplifying test according to an embodiment of the method according to the present invention.
Figure 7B:
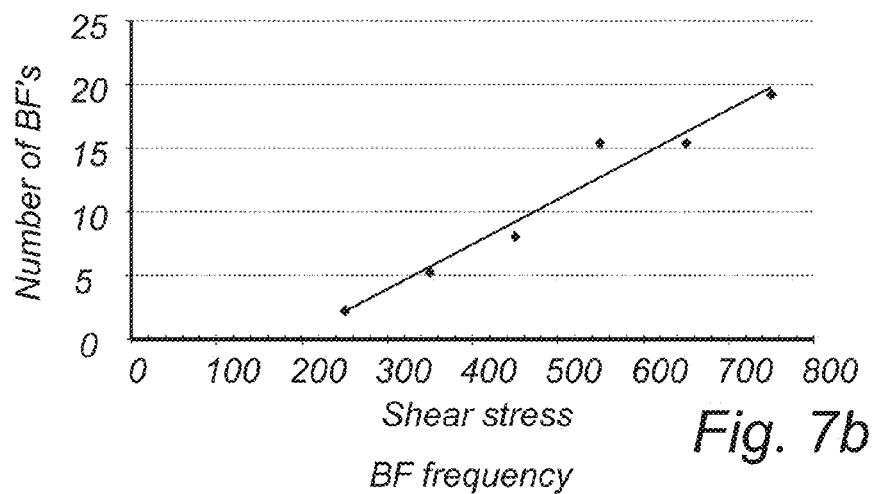
Figure 7C:
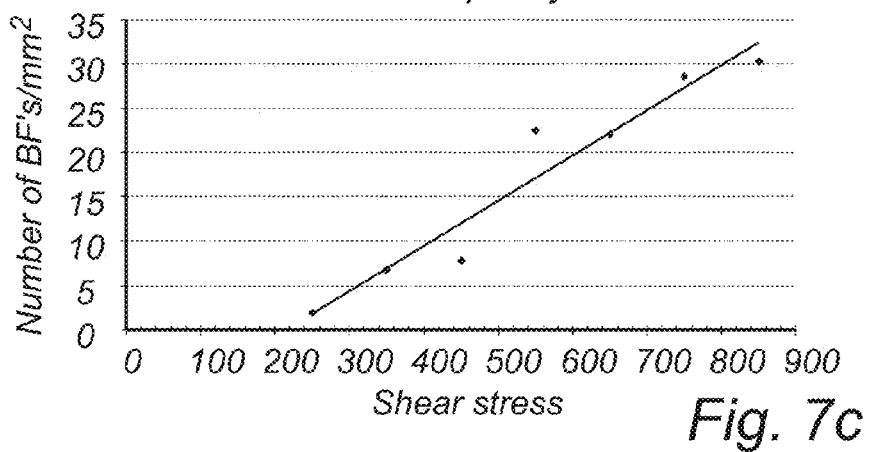
Figure 8A:
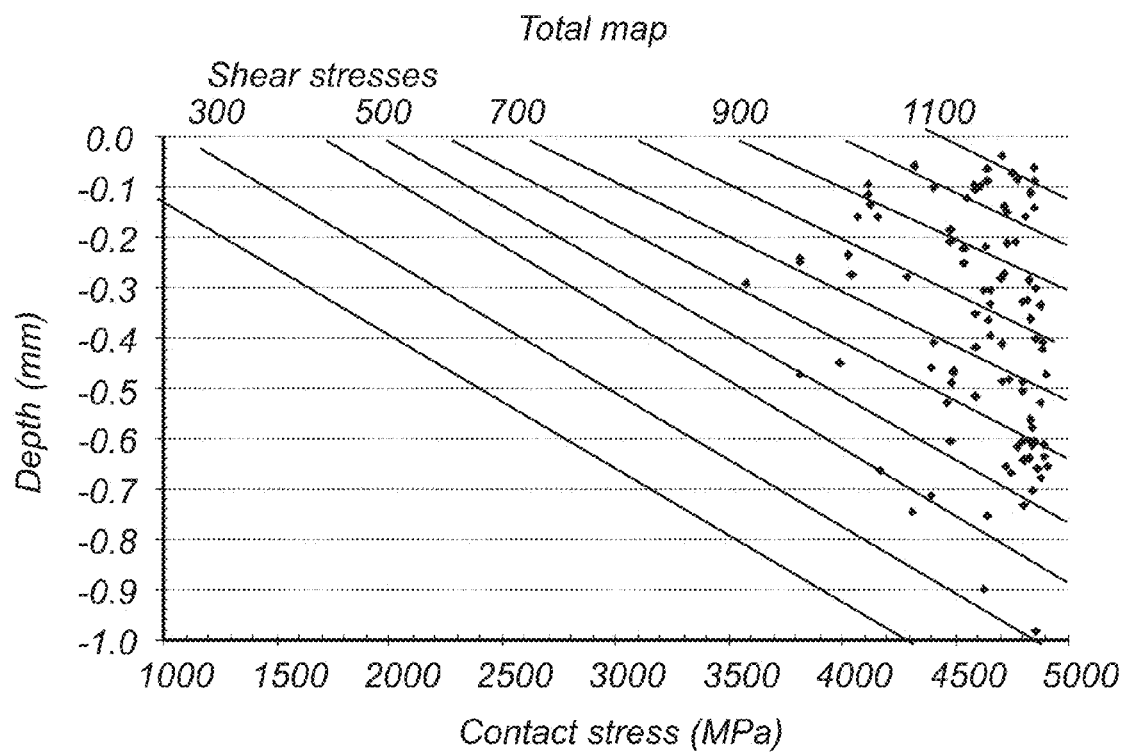
FIG. 8a-b schematically and graphically illustrate data of sub-surface transformations and fatigue limit approximations based on a second exemplifying test according to an embodiment of the method according to the present invention.
Figure 8B:
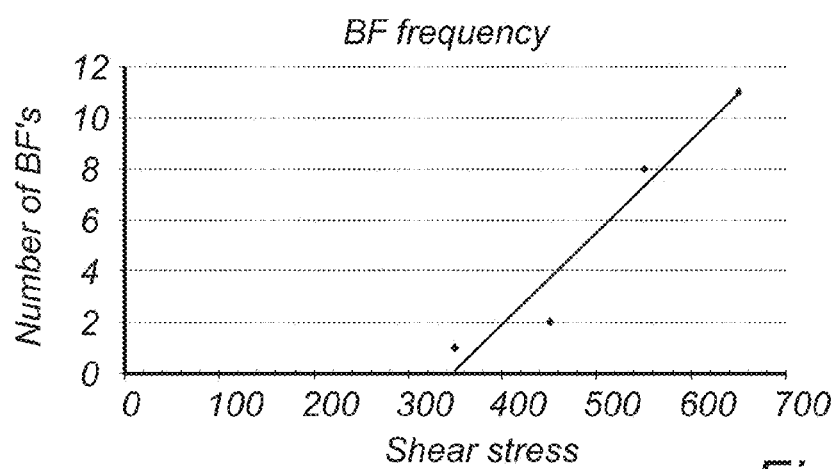

With reference to FIG. 7a-c, test data for a self-aligning ball bearing comprising a poorly hot reduced standard steel is presented, wherein FIG. 8a-b comprise test data for a similar bearing comprising high cleanliness steel with a degree of hot forming reduction.

In FIG. 7a, the data set of sub-surface transformations are plotted in a contact stress/depth diagram together with a determined set of shear intervals of consecutive shear stress level values. In FIG. 7b, a determined frequency parameter value representative of the number of sub-surface transformations situated within each shear interval is plotted, wherein an approximation of the relationship between the shear stress intervals and the number of sub-surface transformation is approximated by curve fitting. In FIG. 7c, the data has be further generalize, wherein the results have been converted into number of sub-surface transformation per unit area of a projection of the examined raceway portion. As an example, the curve fitting based on the exemplifying data provides an estimated fatigue limit value of 220 MPa i.e. the approximated level of zero sub-surface transformations per unit area. The data set of sub-surface transformation for the high cleanliness steel is graphically plotted in a similar manner in FIG. 8a. An analogous analysis of the frequency of sub-surface transformations in relation to shear stress level intervals provides a generalized result of number of transformation per unit area, as illustrated in FIG. 8b. For this bearing, the approximated fatigue limit, calculated in the same way, is increased to 350 MPa.

In exemplifying tests according to embodiments of the method, bearings were run under the same conditions using standard SKF R-2 machines running at 1800 rpm. A pure radial load of 18 kN was mechanically applied for giving an outer ring Po of 4.9 GPa, a C/P of 2.16, an unadjusted L10 life of 10 Mrevs, and an adjusted L10 mh life estimate of 12.8 Mrevs. A circulating oil lubrication system was used with Shell Turbo 100 as lubricant.

Figure 9:
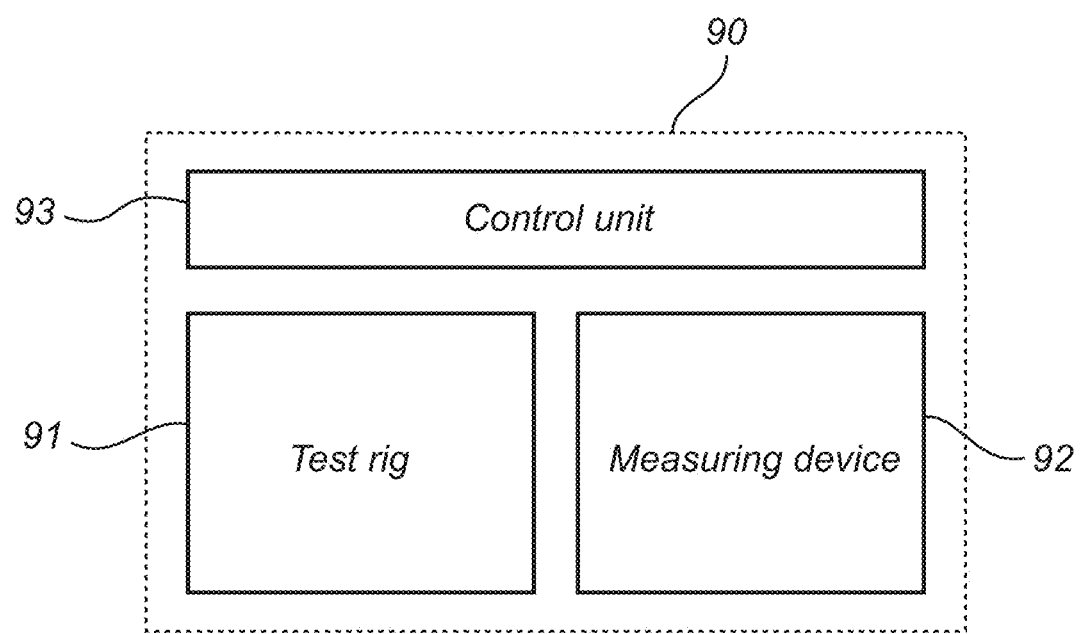
FIG. 9 schematically illustrates an embodiment of an apparatus arrangement according to the present invention.

The bearing outer ring operating temperature was maintained at 70-80° C. giving a kappa value K" of 2.61. The tests were monitored by a sensitive envelope system, and were run to the occurrence of spalling, or to intentional suspension. An exemplifying apparatus arrangement 90 for testing a rolling bearing is schematically illustrated in FIG. 9, which apparatus arrangement 90 comprises a test rig 91 arranged to exert a load on a rolling bearing during test running, a measuring device 92 arranged to identify a set of sub-surface transformations generated during the test run, and a control unit 93 configured, or instructed, to collect parameters values and to determine a fatigue parameter value representative of a predicted fatigue limit. The control unit 93 may e.g. comprises a microprocessor and a storing device, or an operator performing fatigue limit predictions.

It is noted that the invention has mainly been described above with reference to a few embodiments. However, as is readily appreciated by a person skilled in the art, other embodiments than the ones disclosed above are equally possible within the scope of the invention, as defined by the appended patent claims. It is further noted that, in the claims, the word "comprising" does not exclude other elements or steps, and the indefinite article "a" or "an" does not exclude a plurality. A single apparatus or other unit may fulfill the functions of several items recited in the claims. The mere fact that certain measures are recited in mutually different dependent claims does not indicate that a combination of these measured cannot be used to advantage. It is noted, that the method and apparatus arrangement according to the invention may be executed and operated in different orders.

The invention claimed is:

1. A method for determining a fatigue limit for rolling contact initiated fatigue of a rolling bearing, the method comprising:
    running a rolling bearing, having a plurality of rolling elements arranged between an outer and an inner ring, wherein the rolling bearing is exerted to a load which generates sub-surface transformations in a rolling element contact zone of the outer or inner ring, and
    identifying a set of sub-surface transformations in the contact zone along a raceway portion of the rolling bearing, and
    measuring, for each sub-surface transformation in the raceway portion, a position parameter value representative of sub-surface depth and a stress parameter value representative of contact stress in the contact zone, wherein the method further comprises:
    generating a data set of sub-surface transformations comprising the position parameter values in relation to the stress parameter values for each sub-surface transformation,
    determining a fatigue parameter value representative of a predicted fatigue limit for the rolling bearing based on the generated data set of sub-surface transformations,
    determining at least one shear stress level parameter value representative of shear stress in the contact zone, wherein the shear stress level parameter value depends on contact zone depth and exerted contact stress, and
    comparing the at least one shear stress level parameter value with the data set of sub-surface transformations.

2. The method according to claim 1, wherein the fatigue parameter value is determined based on a shear stress level parameter value below which none of the sub-surface transformations generated during running of the rolling bearing are formed.

3. The method according to claim 1, wherein the step of determining the fatigue parameter value further comprises:
    determining a set of shear intervals of consecutive shear stress level values,
    determining, for each shear interval, a frequency parameter value representative of the number of sub-surface transformations situated within each shear interval, and
    estimating the fatigue parameter value by approximating the relationship between the set of shear intervals and the frequency parameter.

4. The method according to claim 1, wherein the exerted load develops a rolling contact stress above 3000 MPa.

5. The method according to claim 1, wherein the load is a radial point load.

6. The method according to claim 5, wherein the raceway portion comprises a maximum load point, and
    wherein the raceway portion extends, from the maximum load point, at least one quarter of the complete raceway.

7. The method according to claim 1, wherein the load is fixed in relation to the rolling element contact zone.

8. The method according to claim 1, further comprises cutting through, or grinding through to, the contact zone along the raceway, wherein a cut surface coincides with a geometrical plane having a normal direction coinciding with an axial direction of the rolling bearing.

9. The method according to claim 8, wherein the steps of identifying and measuring the sub-surface transformation comprises visual or optical inspection.

10. The method according to claim 1, further comprising, monitoring the occurrence of fatigue failure during running of the rolling bearing, and running the rolling bearing until a predetermined fatigue failure parameter is reached.

11. The method according to claim 1, wherein the rolling bearing is a self-aligning ball bearing.

12. A method for determining a fatigue limit for rolling contact initiated fatigue of a rolling bearing, the method comprising:
    running a rolling bearing, having a plurality of rolling elements arranged between an outer and an inner ring, wherein the rolling bearing is exerted to a load which generates sub-surface transformations in a rolling element contact zone of the outer or inner ring, and
    identifying a set of sub-surface transformations in the contact zone along a raceway portion of the rolling bearing, and
    measuring, for each sub-surface transformation in the raceway portion, a position parameter value representative of sub-surface depth and a stress parameter value representative of contact stress in the contact zone, wherein the method further comprises:
    generating a data set of sub-surface transformations comprising the position parameter values in relation to the stress parameter values for each sub-surface transformation, and
    determining a fatigue parameter value representative of a predicted fatigue limit for the rolling bearing based on the generated data set of sub-surface transformations,
    determining at least one shear stress level parameter value representative of shear stress in the contact zone, wherein the shear stress level parameter value depends on contact zone depth and exerted contact stress,
    comparing the at least one shear stress level parameter value with the data set of sub-surface transformations,
    determining a set of shear intervals of consecutive shear stress level values,
    determining, for each shear interval, a frequency parameter value representative of the number of sub-surface transformations situated within each shear interval, and
    estimating the fatigue parameter value by approximating the relationship between the set of shear intervals and the frequency parameter.

13. The method according to claim 12, wherein the fatigue parameter value is determined based on a shear stress level parameter value below which none of the sub-surface transformations generated during running of the rolling bearing are formed.

14. The method according to claim 12, further comprising, monitoring the occurrence of fatigue failure during running of the rolling bearing, and running the rolling bearing until a predetermined fatigue failure parameter is reached.

15. The method according to claim 12, wherein the exerted load develops a rolling contact stress above 3000 MPa.

16. The method according to claim 12, wherein the load is a radial point load.

17. The method according to claim 12, wherein the load is fixed in relation to the rolling element contact zone.

18. The method according to claim 12, wherein the raceway portion comprises a maximum load point, and
wherein the raceway portion extends, from the maximum load point, at least one quarter of the complete raceway.

19. A method for determining a fatigue limit for rolling contact initiated fatigue of a rolling bearing, the method comprising:
running a rolling bearing, having a plurality of rolling elements arranged between an outer and an inner ring, wherein the rolling bearing is exerted to a load which generates sub-surface transformations in a rolling element contact zone of the outer or inner ring, and
identifying a set of sub-surface transformations in the contact zone along a raceway portion of the rolling bearing, and
measuring, for each sub-surface transformation in the raceway portion, a position parameter value representative of sub-surface depth and a stress parameter value representative of contact stress in the contact zone, wherein the method further comprises:
generating a data set of sub-surface transformations comprising the position parameter values in relation to the stress parameter values for each sub-surface transformation,
determining a fatigue parameter value representative of a predicted fatigue limit for the rolling bearing based on the generated data set of sub-surface transformations,
monitoring the occurrence of fatigue failure during running of the rolling bearing, and running the rolling bearing until a predetermined fatigue failure parameter is reached.

20. The method according to claim 19, wherein the fatigue parameter value is determined based on a shear stress level parameter value below which none of the sub-surface transformations generated during running of the rolling bearing are formed.

* * * * *